United States Patent [19]

Rosebrough

[11] Patent Number: 5,807,879
[45] Date of Patent: Sep. 15, 1998

[54] BIOTINIDASE-RESISTANT BIOTINYLATED COMPOUND AND METHODS OF USE THEREOF

[75] Inventor: Scott F. Rosebrough, Avon, N.Y.

[73] Assignee: University of Rochester, Rochester, N.Y.

[21] Appl. No.: 221,113

[22] Filed: Mar. 31, 1994

Related U.S. Application Data

[63] Continuation-in-part of Ser. No. 845,416, Mar. 3, 1992, Pat. No. 5,326,778.
[51] Int. Cl.$^6$ .......................... A61K 31/41; C07D 235/00
[52] U.S. Cl. ..................... 514/387; 548/304.1; 424/1.49; 424/9.362; 424/9.363
[58] Field of Search .......................... 548/304.1; 514/387; 424/1.49, 9.362, 9.363

[56] References Cited

U.S. PATENT DOCUMENTS

| | | | |
|---|---|---|---|
| 2,519,530 | 8/1950 | Wolf et al. | 548/304.1 |
| 4,454,106 | 6/1984 | Gansow et al. | 424/1.1 |
| 4,680,338 | 7/1987 | Sundoro et al. | 525/54.1 |
| 4,863,713 | 9/1989 | Goodwin et al. | 424/1.1 |
| 4,888,163 | 12/1989 | Kubodera et al. | 424/1.1 |
| 4,943,427 | 7/1990 | Yazaki et al. | 424/1.1 |
| 5,504,091 | 4/1996 | Molnar-Kimber et al. | 514/291 |
| 5,578,287 | 11/1996 | Theodore et al. | 424/1.49 |

FOREIGN PATENT DOCUMENTS

| | | |
|---|---|---|
| 3629194 | 3/1987 | Germany . |
| 63-246382 | 10/1988 | Japan . |
| WO/8907097 | 8/1988 | WIPO . |
| 9325668 | 12/1993 | WIPO . |

OTHER PUBLICATIONS

Hnatowich et al. (1987) "Investigations of Avidin and Biotin for Imaging Applications", *J. Nucl. Med.* 28, 1294–1302. Aug.

Kalofonos et al. (1990) "Imaging of Tumor in Patients with Indium–111–Labeled and Streptavidin–Conjugated Antibodies: Preliminary Communication", *J. Nucl. Med. 31*, 1791–196. Nov.

Ohmono et al. (1982) "$^{67}$Ga–Labeled Human Fibrinogen: A New Promising Thrombus Imaging Agent", *Eur. J. Nucl. Med. 7*, 458–461. (8).

Paganelli et al. (1988) "In vivo Labelling of Biotinylated Monoclonal Antibodies by Radioactive Avidin: A Strategy to Increase Tumor Radiolocalization", *Int. J. Cancer 2*, 121–125. (Month Not Available).

Parker (1990) "Tumour Targeting", *Chemistry in Britain*, 942–945. Oct.

Rosebrough (1993) "Plasma Stability and Pharmacokinetics of Radiolabelled Deferoxamine–Biotin Derivatives", *J. Pharmacol. Exp. Ther.* 265, 408. (Month Not Available ).

Takahashi et al. (1985) "Preparation and Biodistribution of $^{67}$Ga–Labelled Fibrinogen Conjugated with a Water–Soluble Polymer Containing Deferoxamine", Vienna IAEA, 471–482. (Month Not Available).

Weiner et al. (1979) "Relative Stability of In–111 and Ga–67 Desferrioxamine and Human Transferrin Complexes", *Proceedings of the Second International Symposium on Radiopharmaceuticals*, 331–340. Mar.

Yamamoto et al. (1988) "Positive Imaging of Venous Thrombi and Thromboemboli with Ga–67 DFO–DAS–Fibrinogen", *Eur. J. Nucl. Med.* 14, 60–64. (Month Not Available).

Yokoyama et al. (1982) "Deferoxamine, A Promising Bifunctional Chelating Agent for Labeling Proteins with Gallium: Ga–67 DF–HSA: Concise Communication", *J. Nucl. Med.* 23, 909–914. (Month Not Available).

R. Blankenburg et al., Biochemistry, vol. 28, No. 20, @ 1989, pp. 8214–8221.

MacLean et al., J. Chem. Soc. Commun. (1992), 18, pp. 1283–1285.

Ebato et al., Angew. Chem., Int. Ed. Engl. (1992), 31(8), pp. 1087–1090.

Kay et al., Biochem. J. (1992), 283(2), pp. 455–459.

Darst et al., Biophys. J. (1991), 59(2), pp. 387–396.

Bladon et al., Tetrahedron Lett. (1989), 30(11), pp. 1401–1404.

Shao et al., Biochemistry (1989), 28(9), pp. 4077–4083.

Fisher et al. (CA 108:108663), 1988.

Shao et al., J. Biol. Chem. (1987), 262(7), pp. 2968–2972.

Chen et al., Biochemistry (1986), 25(4), 939–944.

Wright et al., J. Amer. Chem. Soc., vol. 73, Sep. 1951, pp. 4144–4145.

Fisher, et al. "Synthetic Inhibitors of Carboxypeptidase N", Adv. Exp. Med. Biol. (1986) pp. 405–410.

*Primary Examiner*—Robert W. Ramsuer
*Assistant Examiner*—Laura L. Stockton
*Attorney, Agent, or Firm*—Scully, Scott, Murphy & Presser

[57] ABSTRACT

The present invention provides biotinylated compounds useful for delivering a molecule to a target site, and methods of making biotinylated compounds. The biotinylated compounds are covalent conjugates of biotin and a diagnostic or therapeutic agent, and are stable to rapid degradation by biotinidase. The compounds of the invention are useful for delivering therapeutic or diagnostic agents to target-bound streptavidin or avidin conjugated cell-targeting agents, including monoclonal antibodies. The compound N-cysteinyl biotin is also provided.

25 Claims, 6 Drawing Sheets

BIOTINIDASE-RESISTANT BIOTINYLATED COMPOUND AND METHODS OF USE THEREOF

CROSS REFERENCE TO RELATED APPLICATION

This is a continuation in part of U.S. application Ser. No. 07/845,416 filed Mar. 3, 1992 now U.S. Pat. No. 5,326,778.

This invention was made with government support under Contract No. HL-24230-11 awarded by the National Institutes of Health. The government has certain rights in the invention.

FIELD OF THE INVENTION

The present invention provides biotinylated compounds useful for delivering a molecule to a target site. In particular, the present invention is directed to covalent conjugates of biotin and a diagnostic or therapeutic agent, wherein the conjugates are stable in vivo due to a biotinidase-resistant linkage. In a two-step approach, biotin conjugates are used to deliver radionuclides, cytotoxic drugs, MRI agents, fluorochromes and other agents suitable for imaging and therapy to target-bound streptavidin or avidin conjugated antibodies or other targeting agents. The present invention further provides N-cysteinyl biotin, and a method of making the biotinylated compounds of the invention.

BACKGROUND OF THE INVENTION

Various diagnostic therapeutic fluorescent and enzyme linked applications utilize cell or tissue specific targeting agents as delivery systems for radioactive, paramagnetic, cytotoxic or therapeutic agents. Any agent which is specific for a lesion or site of interest can potentially act as a targeting agent. For example, polyclonal and monoclonal antibodies can be produced which exhibit considerable specificity for certain cell or tissue types. Many other agents, including toxins such as diphtheria toxin, exhibit cell specificity and can be used to deliver diagnostic or therapeutic agents. The technique of delivery of monoclonal antibodies (MAbs) has been investigated for cancer therapy as well as for diagnosis of cancer, thromboembolism and cardiac myopathy. For successful radioimmunoimaging, sufficient labeled MAb must localize at the target site to provide enough signal for detection. Target-to-background ratios must be high in order to achieve adequate contrast between target-bound radioactivity and background levels in other organs, tissues and blood. A major obstacle to successful radioimmunoimaging is the high background activity of free circulating radiolabeled MAbs due to prolonged circulation and accumulation in liver and spleen, the normal metabolic sites for Abs. Furthermore, the toxic effects of high radiation doses must be considered in both radioimmunotherapy and radioimmunoimaging. Such obstacles are also a consideration for methods utilizing targeting agents other than monoclonal antibodies.

To overcome such obstacles, "pre-targeting" or "two-step" approaches have been investigated. In the conventional one-step method the radionuclide is linked to the MAb either directly or via a bifunctional chelating agent. In the two-step approach the antibody is unlabeled. Unlabeled antibody is administered, and antibody which does not localize to the target site is allowed to clear from circulation before the administration of radioactivity. The radioactivity is then administered in a chemical form which has high affinity for the antibody.

To provide the diagnostic or imaging agent in a form with high affinity for the antibody, two-step methods have been designed to exploit the high affinity of avidin and streptavidin for biotin. Avidin, a 67 kilodalton (kD) glycoprotein found in egg whites, has an exceptionally high binding affinity ($K_d=10^{-15}$) for biotin. Avidin consists of four subunits, each capable of binding one biotin molecule. Streptavidin, a similar protein produced in *Streptomyces avidinii*, shares significant conformation and amino acid composition with avidin, as well as high affinity and stability for biotin. However, streptavidin is not glycosylated and reportedly exhibits less non-specific binding to tissues. Streptavidin is widely used in place of avidin because of its lower non-specific binding. Biotin, a member of the B-complex vitamins, is essential for amino acid and odd-chain fatty acid degradation, gluconeogenesis and fatty acid synthesis and is normally found in the enzyme bound form as biocytin.

The use of the two-step avidin-biotin or streptavidin-biotin approach for immunoimaging and immunotherapy is theoretically attractive since: 1) biotin and avidin are likely to be nontoxic at the levels required for these applications; 2) the high affinity of avidin and biotin results in the in vivo stability of the avidin-biotin bond; 3) the rapid clearance of biotin through the kidney avoids problems associated with use of radiolabeled MAbs; and 4) the tetravalency of avidin and streptavidin for biotin allows for amplification of the signal at the target site.

In the two-step avidin-biotin or streptavidin-biotin approach, antibodies are coupled with either biotin or avidin and administered to the subject, followed by administration of radiolabeled avidin or biotin, respectively. Using an animal non-tumor model, Hnatowich et al. [(1987) *J. Nucl. Med.* 28, 1294] have demonstrated the administration of avidin-conjugated antibody to mice, followed by administration of $^{111}$In-labeled biotin. Imaging was performed to determine the ratio of radioactivity in the target organ relative to other organs. Using Protein A-conjugated beads to simulate tumor, Hnatowich et al. thus demonstrated localization of the label to the target, with improved target-to-nontarget ratios relative to the conventional one-step approach. In a similar study, Paganelli et al. [(1988) *Int. J. Cancer* 2, 121] demonstrated the in vivo labeling of biotinylated antibody with $^{131}$I-and $^{111}$In-labeled avidin.

Kalofonos et al. [(1990) *J. Nucl. Med.* 31, 1791] have reported preliminary results of a limited clinical trial in which patients with squamous cell carcinoma of the lungs received streptavidin-conjugated monoclonal antibody followed by $^{111}$In-labeled biotin. In eight out of ten patients, tumor was detected with labeled biotin alone without the previous administration of streptavidin-conjugated antibody, perhaps due to localization of labeled biotin in tumor. In three of these patients, images were improved with the prior administration of antibody. The fact that targeting was not improved in all patients was speculated to be due to rapid internalization of antibody but may be the result of uptake of biotin by tumor cells.

Clinical studies demonstrating a two-step approach (biotinylated MAb followed by $^{111}$In-labeled streptavidin) and a three-step approach (biotinylated MAb followed by cold avidin followed by $^{111}$In-labeled biotin) have also been reported by Paganelli et al. [(1990) *J. Nucl. Med.* 31, 735].

In the above studies, biotin, avidin and streptavidin were each labeled with $^{111}$In via the bifunctional chelating agent diethylenetriaminepentaacetic acid (DTPA) by the bicyclic -nhydride method of Hnatovich et al. [(1982) *Int. J. Appl.*

*Radiat. Isotop.* 33, 327]. DTPA-biotin is prepared by covalently linking DTPA to biotin through the use of the cyclic anhydride of DTPA and biocytin, a lysine conjugate of biotin with an available primary amine for conjugation (Hnatowich, 1987).

Biocytin is a lysine conjugate of biotin which is the main form of biotin in foodstuffs, and is useful for synthesis of biotin derivatives since it is readily conjugated due to the availability of a primary amine. Biocytin is commercially available in its N-protected form as succinimidyl-6-(biotinamide)hexanoate (NHS-LC-biotin). NHS-LC-biotin has been considered the reagent of choice for biotinylation reactions. (Diamandis et al., 1991, *Clin. Chem.* 37:625.) However, it has been discovered in accordance with the present invention that conjugates of biocytin are unstable in vivo and therefore unsuitable for in vivo uses including two-step imaging and therapy. Specifically, biotin conjugates prepared via NHS-LC-biotin are rapidly degraded, and the site of cleavage mimics the site in biocytin at which digestion by biotinidase occurs. Biotinidase is an enzyme found in high concentrations in plasma, gut, liver and other tissues which catalyzes the hydrolysis of biocytin to biotin and free lysine as follows:

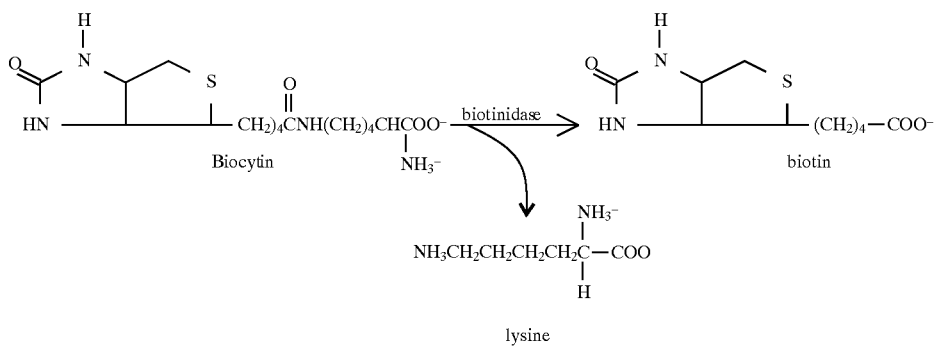

Biotinidase also digests short biotinyl peptides. It has been demonstrated that biotinidase is not a general proteolytic enzyme, but rather has specific structural requirements in the substrate for hydrolysis [Chauhan et al. (1986) *J. Biol. Chem.* 261, 4268].

The present invention overcomes the deficiencies of the prior art by providing biotinylated compounds that are not subject to rapid degradation by biotinidase.

SUMMARY OF THE INVENTION

This invention relates to biotinidase-resistant biotinylated compounds containing a chemical fragment having the structure:

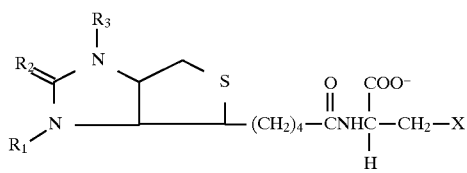

wherein $R_1$ and $R_3$ are independently hydrogen, carboxyl or lower alkyl and $R_2$ is O or NH and X is S or a chemical bond. The biotinylated compounds of the present invention are stable in vivo and capable of binding avidin and streptavidin.

In a preferred embodiment, the chemical fragment has the structure:

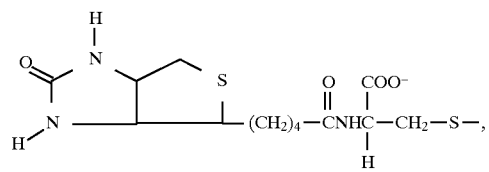

and is covalently bound, directly or by a linker to a moiety which is useful in diagnosis or therapy. In a preferred embodiment, the moiety is a chelating agent, a halogenating agent, a toxin, a chemotherapeutic drug, a fluorophore or an enzyme.

The present invention provides biotinylated compounds having the formula:

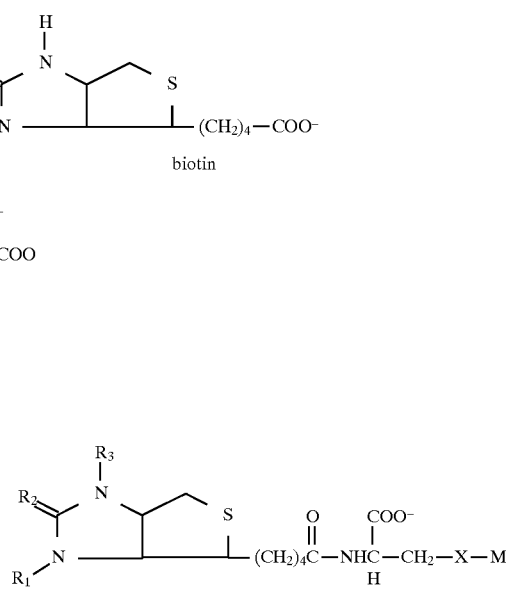

wherein the negative charge on the carboxylate is balanced by a cation and wherein $R^1$ and $R^3$ are independently hydrogen, carboxyl or lower alkyl; $R_2$ is O or NH; X is a chemical bond or a linking group and M is a diagnostic or therapeutic moiety. In a preferred embodiment, $R_1$ and $R_3$ are H, $R_2$ is O, X is S-Y wherein Y is a chemical bond, acetyl or a C1–C6 alkylene chain, and M is a chelating agent, a halogenating agent, a toxin, a chemotherapeutic drug, a fluorophore or an enzyme.

The present invention further provides the biotinylation reagent N-cysteinyl-biotin.

A further aspect of the present invention provides a method for biotinylating a molecule wherein said method comprises reacting the molecule with N-cysteinyl-biotin.

A further aspect of the present invention provides a method of delivering a diagnostic or therapeutic agent to a target site. The method of delivery of a diagnostic agent comprises administering an avidin or streptavidin conjugated targeting agent to a host in an amount sufficient to bind to a target site, followed by administering a detectable biotinylated compound of the present invention under conditions to form a complex with said avidin or streptavidin conjugated targeting agent and at a dose sufficient for detection. The resulting complex is then detected. In a preferred embodiment the targeting agent is an antibody or antibody fragment.

The method of delivery of a therapeutic agent comprises administering an avidin or streptavidin conjugated targeting agent to a host in an amount sufficient to bind to the target site, followed by administering a biotinylated compound of the present invention at a therapeutic dose and under conditions to form a complex with said avidin or streptavidin conjugated targeting agent. In a preferred embodiment the targeting agent is an antibody or antibody fragment.

Yet another aspect of the present invention provides pharmaceutical compositions containing the subject biotinylated compounds and a pharmaceutically acceptable carrier.

A compartmentalized kit fr imaging or therapy is also provided by the present invention.

DETAILED DESCRIPTION OF THE INVENTION

Figure 1:
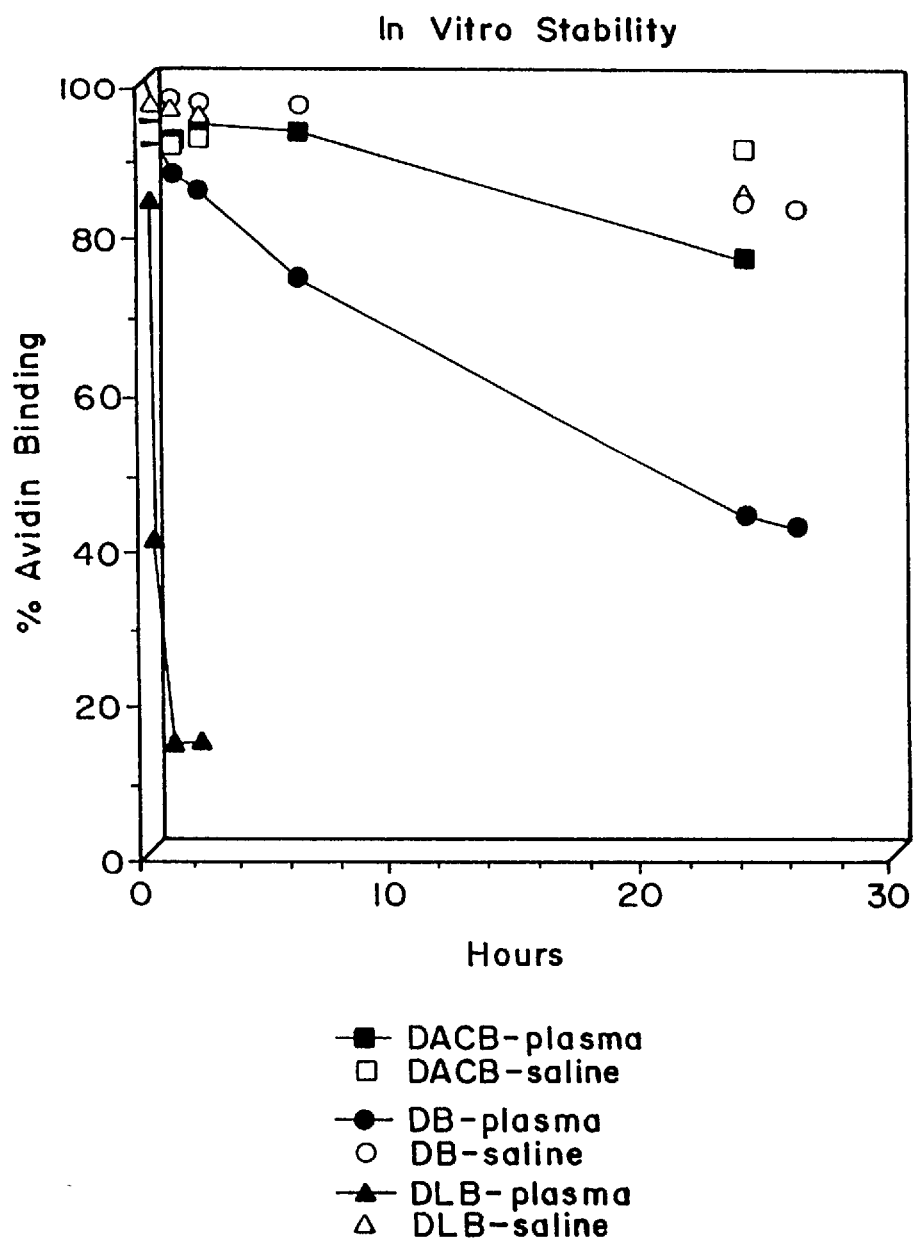
FIG. 1 is a graph of the percent of avidin binding ability retained in vitro by Defero-Acetyl-Cysteinyl-Biotin (DACB), Deferobiotin (DB) and Defero-Desaminolysyl-Biotin (DLB) following incubation in saline and plasma.

The present invention is directed to biotinylated compounds that are stable in vivo, and capable of stably binding avidin and streptavidin. The biotinylated compounds of the present invention contain a chemical fragment having the structure:

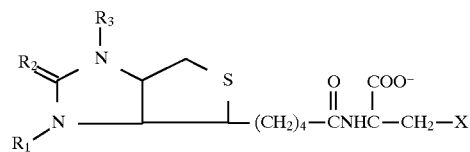

wherein $R_1$ and $R_3$ are independently hydrogen, carboxyl or lower alkyl, $R_2$ is O or NH, and X is S or a chemical bond.

In a preferred embodiment the fragment has the structure:

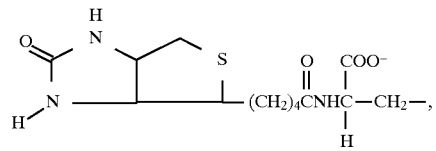

In a more preferred embodiment the fragment has the structure:

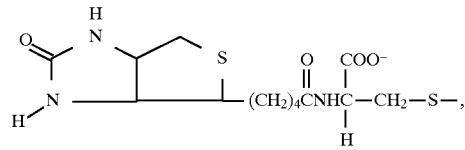

As used herein, compounds that are "biotinidase-resistant" and "stable in vivo" are defined as those compounds that maintain greater than 50% of avidin binding ability and the functional activity of the moiety that has been biotinylated after incubation in plasma for six hours, relative to unincubated compounds, as measured by the avidin binding assay as described hereinbelow.

It has been discovered in accordance with the present invention that biotinylated compounds of the prior art, and in particular compounds synthesized utilizing the biotinylating reagent NHS-LC-biotin, are particularly susceptible to cleavage by biotinidase, and thus are unsuitable for in vivo applications. For example, biotinylation of the metal chelating agent deferoxamine via NHS-LC-biotin according to Scheme I results in the synthesis of defero-desaminolysyl-biotin (DLB) as follows:

Scheme I

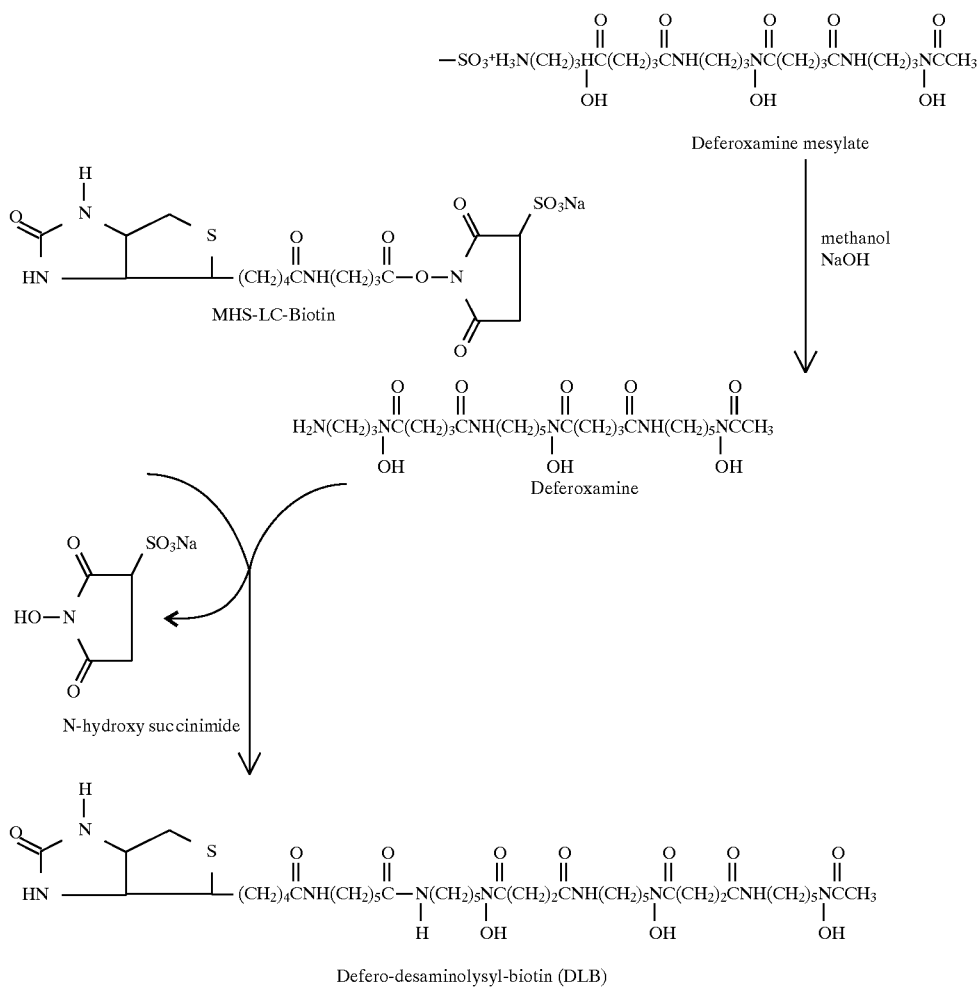

Chromatographic analysis of $^{67}$Ga-labeled DLB after incubation in plasma at 37° C. for two hours, or after intravenous injection into experimental animals, indicates that DLB is rapidly degraded in vivo to biotin and desaminolysyl-deferoxamine.

It has been discovered in accordance with the present invention that a novel linkage between biotin and the functional moiety to be biotinylated renders the compounds of the present invention stable in vivo. In particular, the presence of a carboxyl group adjacent to the amide cleavage site for biotinidase renders the compounds of the present invention resistant to cleavage by biotinidase. Accordingly, the biotinylated compounds of the present invention have the formula:

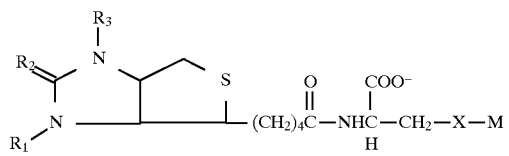

wherein the negative charge on the carboxylate is balanced by a cation and wherein $R_1$ and $R_3$ are independently hydrogen, carboxyl or lower alkyl; $R_2$ is O or NH; X is a chemical bond or a linking group; and M is a diagnostic or therapeutic moiety. In a preferred embodiment $R_1$ and $R_3$ are hydrogen, $R_2$ is oxygen, X is S-Y wherein Y is a chemical bond, acetyl, or a C1–C6 alkylene chain; and M is a chelating agent, a halogenating agent, a toxin, a chemotherapeutic drug, a fluorophore or an enzyme. In a most preferred embodiment the alkylene chain is C1–C3. Lower alkyl refers to C1–C6.

Diverse classes of compounds, including proteins, polysaccharides, nucleic acids, haptens, peptides, chelating agents, halogenating agents, enzymes, fluorophores, lectins, cytotoxins, and drugs have been biotinylated in the prior art for a variety of applications. (See e.g. Diamandis et al., 1991, Clin. Chem. 37:625.) The present invention is an improvement over the available technology in that the novel linkage of the biotinylated compounds of the present invention renders the present compounds stable in vivo. The present invention is applicable to the biotinylation of any and all of the above-listed moieties. In a preferred embodiment the moiety to be biotinylated is a metal chelating agent. Particularly preferred metal chelating agents include deferoxamine (DFO), diethylenetriaminopenta-acetic acid (DTPA), ethylenediaminetetra-acetic acid (EDTA), bis-aminothiol (BAT, $N_2S_2$), ethylenediamine-di(O-hydroxyphenylacetic acid) (EDHPA), 2,2-dipyridyl (DIPY), polyaminopolycarboxylate, tetra-azacyclododecane tetraacetate (DOTA), dithiocarbamate, dithiosemicarbazone (DTS), tetraazacyclotetradecanetetracetate (TETA), hydroxamic acid derivatives and porphyrins. In a preferred embodiment the metal chelating agent is complexed with a metal. In a most preferred embodiment the metal is Tc-99m, $^{67}$Ga, $^{68}$Ga, $^{111}$In, $^{90}$Y, $^{186}$Re, $^{188}$Re, $^{212}$Bi, Fe, $^{52}$Fe or Gd.

In another preferred embodiment the moiety to be biotinylated is a halogenating agent. Particularly preferred halogenating agents include tyramine, aniline, Bolton Hunter reagent and stannane. In an especially preferred embodiment the halogenating agent is radiohalogenated with an isotope of chlorine, bromine, iodine, fluorine or astatine. $^{211}$At, $^{77}$Br, $^{123}$I, $^{125}$I and $^{131}$I are most preferred. In another preferred embodiment the moiety to be biotinylated is a fluorophore. Particularly preferred fluorophores are fluorescein, coumarin, rhodamine, phycoerythrin and Texas Red.

Preferred toxins include abrin, ricin, modeccin, Pseudomonas exotoxin A, diphtheria toxin, pertussis toxin and Shiga toxin. Preferred enzymes include alkaline phosphatase, horseradish peroxidase, β-galactosidase and glucose oxidase. Preferred therapeutic drugs include methotrexate, vinblastine, doxorubicin, bleomycin, cisplatinum, urokinase and tissue plasminogen activator.

The biotinylated compounds of the present invention can be synthesized by derivatizing biotin or a biotin derivative of the formula:

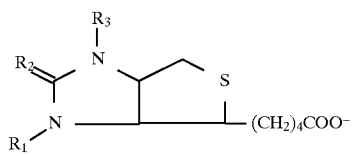

wherein the nagtive charge on the carboxylate is balanced by a cation and wherein $R_1$ and $R_3$ are independently hydrogen, carboxyl or lower alkyl; $R_2$ is O or NH; or a commercially available biotin analog, for example NHS-biotin or sulfo-NHS-biotin, to provide an intermediate comprising a fragment having the formula:

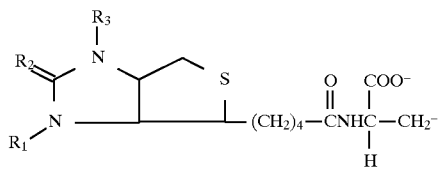

wherein $R_1$ and $R_3$ are independently hydrogen, carboxyl or lower alkyl and $R_2$ is O or NH.

Modifications of the biotin molecule that retain avidin and streptavidin binding ability are well known to the ordinarily skilled artisan and are within the scope of this invention, and are exemplified by substituents $R_1$, $R_2$ and $R_3$. In addition, the biotin molecule can be modified to bind modified avidin and streptavidin molecules. For example, a biotin modified at the ring sulfur by oxidation can bind to a suitably modified avidin or streptavidin. Biotin modifications that result in ring openings are also contemplated.

The above intermediate can be prepared by synthetic methods known to the ordinarily skilled artisan. In a preferred embodiment, the intermediate is prepared by reacting a commercially available form of biotin, NHS-biotin, or its water soluble analog, sulfo-NHS-biotin, with a compound comprising the group

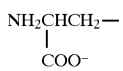

under conditions to form an amide bond with biotin, i.e., to form a compound comprising the fragment:

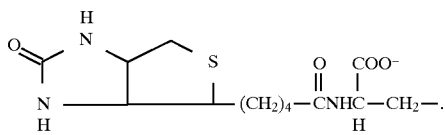

wherein the negative charge is balanced by a cation.

In a more preferred embodiment, NHS-biotin or sulfo-HS-biotin is reacted with cysteine to provide N-cysteinyl-biotin:

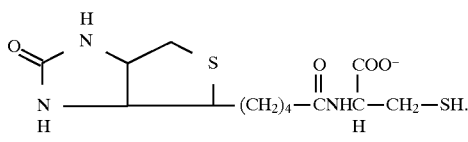

For example, to prepare cysteinyl-biotin, cysteine is added to 0.05M phosphate buffer, pH 12 containing a concentration of dithiothreitol (DTT) at least equimolar to cysteine. 60–120 mM DTT is added to cysteine in 0.005M phosphate buffer for a final concentration of 60 mM cysteine. NHS-biotin is solubilized in methanol at a concentration of 20 mM and heated to 60°. Equal volumes of the cysteine and NHS-biotin solutions are mixed and incubated at 65°. The preferred molar ratio of cysteine:NHS-biotin is 2–10:1. The fraction containing cys-biotin can be identified by its reactivity with 5,5'- dithiobis-(2-nitrobenzoic acid), (DTNB; Ellman's reagent). Ellman's reagent is used to detect thiols and reacts with cys-biotin but not with free biotin, which does not contain a free SH group.

The intermediate compound comprising the fragment:

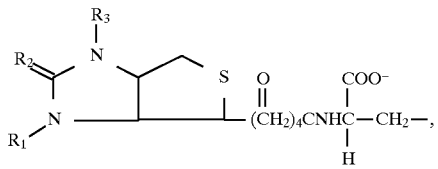

for example N-cysteinyl biotin, is used to biotinylate any molecule of interest. The chemistry of the biotinylation reaction is determined by the nature of the reactive group on the molecule to be biotinylated, and can be performed by standard synthetic methods known to one of ordinary skill in the art.

Either or both of the intermediate compound and the olecule to be biotinylated may be derivatized with a reactive group to facilitate the biotinylation reaction. For example, cysteinyl biotin can be reacted with a variety of compounds, for example ethylenediamine or N-(iodoethyl) trifluoroacetamide(Aminoethyl-8) to form an intermediate with a reactive amine for conjugation to the molecule to be biotinylated. For example, the reaction of N-cysteinyl-biotin and N-(idoethyl)tri-fluoro-acetamide (Aminoethyl-8) for 12 hours at 50° C., pH 8.5 at a molar ratio of 20:1 (Aminoethyl-8: biotin cysteine) provides the intermediate:

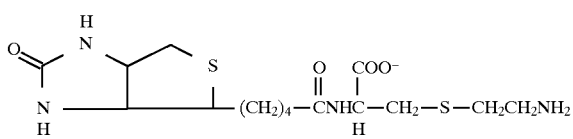

Such intermediates can be used for example to biotinylate molecules with available carboxylic acid derivative moieties by nucleophilic substitution reactions known to one of ordinary skill in the art. Similarly, the biotincontaining intermediate of the present invention can be derivatized to provide any appropriate reactive group or moiety, for example tyrosyl, histidyl, sulfhydryl, carboxyl or hydroxyl group in order to facilitate covalent bonding to the molecule to be biotinylated by methods known to one of ordinary skill in the art.

The molecule to be biotinylated can also be derivatized by methods known to one of ordinary skill in the art. For example, reaction of the metal chelating agent deferoxamine with iodoacetic acid N-hydroxysuccinimide ester (NHS-IA) for 1 hour at 65° C. at a molar ratio of 2–10:1 (NHS-IA:DFO) provides the compound idoacetyl-deferoxamine:

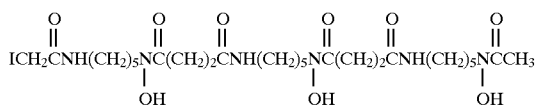

which can be directly reacted with N-cysteinyl biotin to provide biotinylated deferoxamine in accordance with the present invention. The biotinylated deferoxamine resulting from the conjugation of iodoacetyl-deferoxamine and cysteinyl biotin is designated defero-acetyl-cysteinyl-biotin (DACB) and has the formula:

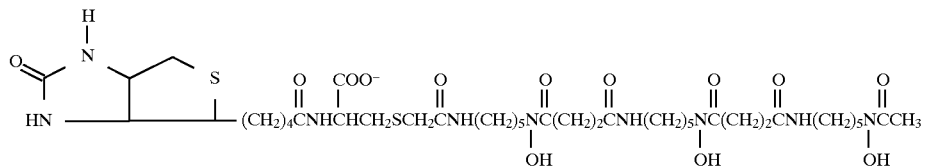

Accordingly, by derivatizing the biotin intermediate of the present invention and/or the molecule to be biotinylated with appropriate functional groups, the ordinarily skilled artisan can use known methods for biotinylation to produced improved biotinylated compounds that are stable to biotinidase. Chemical reactions for biotinylation are known to the skilled artisan, and are the subject of numerous reviews, for example Diamandis et al. (1991) *Clin. Chem.* 37:625, and Wilchek et al. (1990) *Methods in Enzymology* 184:123.

The novel linkage of the biotinylated compounds of he present invention provides a carboxyl group adjacent to the amide cleavage site for biotinidase and renders the biotinylated compounds of the invention resistant to rapid cleavage by biotinidase. As defined in accordance with the present invention, biotinidase resistant compounds maintain greater than 50% of avidin binding ability and the functional activity of the moiety that has been biotinylated after incubation in plasma for six hours, relative to unincubated compounds. The measurement of retention of activity of both moieties of the compounds of the present invention (i.e. biotin and the moiety that has been biotinylated) provides a measurement of the stability of the compounds to biotinidase.

An in vitro avidin binding assay can be used to evaluate avidin binding ability. The functional assay is determined by the nature of the molecule that has been biotinylated. For example, if the moiety is a metal chelating agent, the compound can be labelled with a radioactive metal, and radioactivity of the compound can be detected. Enzymes can be evaluated for example by reactivity with substrates, proteins can be detected by antibody reactivity, and halogenating agents can be labeled with detectable radioactive halogens.

To evaluate stability, the biotinylated compounds of the invention can be incubated in the presence of biotinidase (e.g. in plasma or in vivo) and then incubated with avidin under conditions sufficient for avidin-biotin binding and filtered under conditions such that avidin and the biotinylated compounds of the invention are retained, but nonbiotinylated molecules and free radiometals are not retained. The functional activity, e.g. radioactivity, of the retentate is then measured and compared to the unseparated incubation mixture to provide a measurement of the stability of the biotinylated compounds to biotinidase. Dissociation of the functional moiety from biotin is reflected as decreased functional activity associated with the biotin-avidin complex.

For example, the stability of biotinylated DFO prepared in accordance with the present invention can be assessed as follows.

Radioactive labeling of the DFO-biotin conjugate can be easily accomplished by direct addition of a radioactive metal solution, for example $^{67}$Ga, to the DFO-biotin conjugate, followed by incubation at room temperature for one to several hours. Avidin binding can be accomplished by incubating the radiolabeled DFO-biotin conjugate with an excess of avidin for a time sufficient for avidin-biotin binding (one to several minutes). This binding is most conveniently performed on a filter to effect subsequent separation of avidin and biotin from DFO and small metabolites. In a preferred embodiment, the filter is a Centricon 30 microfiltration device, which will retain avidin and DFO-biotin conjugates but not uncomplexed DFO or free radiometal. With a Centricon 30 filtration device, filtration is accomplished by centrifugation at about 4000–5000×g for about 20–30 minutes. The amount of radioisotope present in the incubation mixture is measured before and after filtration by methods well known to one of ordinary skill in the art and appropriate for the isotope used. For example, $^{67}$Ga is measured by a gamma counter. The ratio of radioactivity present in the unseparated incubation mixture to the radioactivity present in the retentate, i.e. the radioactivity bound to avidin via the DFO-biotin conjugate, provides a measurement of the stability of the DFO-biotin conjugate. For example, a ratio of 0.5 indicates that 50 percent of the radiolabeled conjugated has dissociated. The in vitro stability of the radiolabeled conjugates is assessed by performing the avidin binding assay after incubation of the conjugate in plasma for various amounts of time prior to the avidin binding assay.

To further assess the in vivo stability of the compounds of the present invention, the compounds can be injected into animals. Plasma and urine samples are obtained at various time points and then subjected to the avidin binding assay described above to determine the amount of functional activity that has remained associated with biotin, i.e. the stability of the biotinylated compound in vivo. Plasma and urine samples can also be analyzed, for example by high performance liquid chromatography (HPLC), to determine the presence of the intact biotinylated compound and its metabolites. The chromatographic profiles of plasma and urine samples can be compared to known profiles of the unincubated biotinylated compound, the non-biotinylated functional moiety, or other expected metabolites, to determine whether the biotinylated compound has been degraded. Conditions and methods for HPLC are well known to one of ordinary skill in the art, and chromatographic conditions such as flow rate and gradient program can easily be selected and optimized by the skilled artisan. In a preferred embodiment, reverse phase chromatography is used and a complexing agent is included in the mobile phase to ensure that iron contamination present in buffers or bound to the column does not interfere with analysis. Preferably the complexing agent is nitrilotriacetic acid (NTA) and is present at a concentration of about 2 mM.

For biotinylated compounds comprising a metal-chelating agent, another aspect of the present invention provides the subject compounds labeled with a metal ion. In a preferred embodiment, the metal is paramagnetic or radioactive. All metals capable of forming stable metal chelates with the biotinylated compounds of the present invention are contemplated. In a preferred embodiment, the biotinylated compounds of the present invention are labeled by chelation with Fe, Gd, $^{99m}$Tc, $^{111}$In, $^{67}$Ga, $^{68}$Ga, $^{90}$Y, $^{186}$Re, $^{188}$Re, or $^{212}$Bi. Chelation with metal ions can be accomplished by methods known to one of ordinary skill in the art. For example, the compounds of the present invention can be labeled with $^{67}$Ga by direct addition of a $^{67}$Ga solution to the biotinylated compound, followed by incubation at room temperature for one to several hours.

For biotinylated compounds comprising a halogenating agent, another aspect of the present invention provides the compounds covalently bound to a halogen. In a preferred embodiment the halogen is a radioisotope of chlorine, bromine, iodine, fluorine or astatine. In a more preferred embodiment the halogen is $^{211}$At, $^{77}$Br, $^{123}$I, $^{125}$I, or $^{131}$I. Halogenation can be accomplished by methods known to one of ordinary skill in the art. The halogenating agent can be halogenated before or after biotinylation.

Another aspect of the present invention is directed to a method of delivering a diagnostic or therapeutic agent to a target site. The biotinylated compounds of the present invention provide a delivery system for radioactive or paramagnetic metals, halogens, cytotoxins, chemotherapeutic drugs, fluorophores, enzymes or any other moiety that can be biotinylated by the method of the present invention. The method of delivery of a diagnostic agent comprises administering an avidin or streptavidin conjugated targeting agent to a host in an amount sufficient to bind to a target site, followed by administering a detectable biotinylated compound of the present invention under conditions to form a complex with said avidin or streptavidin conjugated targeting agent and at a dose sufficient for detection. The resulting complex is then detected. In a preferred embodiment the targeting agent is a monoclonal antibody. More preferred targeting agents include humanized or chimeric antibodies, human monoclonal or polyclonal antibodies, $F_v$ fragments, single chain antibodies (SCA), molecular recognition units (MRU) and synthetic genetically engineered binding proteins or peptides.

The method of delivery of a therapeutic agent comprises administering an avidin or streptavidin conjugated targeting agent to a host in an amount sufficient to bind the target site, followed by administering a biotinylated compound of the present invention at a therapeutic dose and under conditions to form a complex with said avidin or streptavidin conjugated targeting agent. In a preferred embodiment the targeting agent is a monoclonal antibody. More preferred targeting agents include humanized or chimeric antibodies, human monoclonal or polyclonal antibodies, $F_v$ fragments, single chain antibodies (SCA), molecular recognition units (MRU) and synthetic genetically engineered binding proteins or peptides.

The two-step approach comprises administering an avidin or streptavidin conjugated targeting agent that is specific for a tissue or lesion of interest to a patient, followed by administering, hours to several days later, the detectable or therapeutically effective biotinylated compound of the present invention. Biotinylated compounds of the present invention that contain a chelating agent are rendered detectable or therapeutic by labeling with a radioactive or paramagnetic metal. For radioimaging of a tissue or lesion of interest, it is preferred that the biotinylated compound is labeled with Fe, Gd, $^{52}$Fe, $^{68}$Ga, $^{99m}$Tc, $^{111}$In, or $^{67}$Ga. For radioimmunotherapy, it is preferred that the DFO-biotin conjugate is labeled with $^{186}$Re, $^{188}$Re, $^{212}$Bi or $^{90}$Y. In radioimmunoimaging applications, administration of the labeled biotinylated compound is followed by detection of the complex. The method used for diagnostic imaging is appropriate for the particular metal in the compound. For example, paramagnetic metal ions such as Fe and Gd are suitable for nuclear magnetic resonance (NMR) analysis or magnetic resonance imaging (MRI). $^{52}$Fe and $^{68}$Ga are appropriate for analysis by positron emission tomography (PET), whereas $^{99m}$Tc, $^{111}$In and $^{67}$Ga can be detected by gamma camera imaging. The aforementioned means of image analysis are known to one of ordinary skill in the art and can be conducted in accordance with well-established techniques.

Biotinylated compounds of the present invention that contain a halogenating agent may be rendered detectable or therapeutic by labeling with a radioactive halogen. Preferred radioactive halogens include $^{211}$At, $^{123}$I, $^{125}$I and $^{131}$I. Methods for detecting halogens are known to one of ordinary skill in the art.

Similarly, the method of detection of other biotinylated compounds of the present invention is dictated by the nature of the moiety that has been biotinylated. Detection is accomplished by methods known to one of ordinary skill in the art.

In the method of delivery of the present invention, compounds can be administered by well-known routes including oral, intravenous, intramuscular, intranasal, intradermal, subcutaneous, parenteral and the like. Dosage of the targeting agents and biotinylated compounds of the present invention is an amount sufficient for the desired therapeutic or diagnostic effect.

In a preferred embodiment, the two-step radioimaging and radiotherapy methods described above utilize avidin or streptavidin conjugated polyclonal or monoclonal antibodies as the targeting agent. Antibodies contemplated by the present invention include anti-tumor antibodies, anti-fibrin antibodies, anti-myosin antibodies and any lesion-specific antibodies. Anti-fibrin and anti-myosin antibodies are particularly useful in cardiac imaging. Non-specific IgG is also useful in accordance with the present invention since it can be used in targeting of abscesses via Fc receptor binding. More preferred targeting agents include humanized or chimeric antibodies, human monoclonal or polyclonal antibodies, $F_v$ fragments, single chain antibodies (SCA), molecular recognition units (MRU) and synthetic genetically engineered binding proteins or peptides. Standard methods for the production and purification of antibodies and antibody fragments are known to one of ordinary skill in the art and can be found, for example, in *Antibodies: A Laboratory Manual*, Harlow et al., eds, (1988) Cold Spring Harbor Laboratory. Methods for conjugating avidin or streptavidin to monoclonal antibodies are known to one of ordinary skill in the art. For example, Kalofonos et al. (1990) and Hnatowich et al. (1987) disclose methods for conjugating an antibody with streptavidin and avidin, respectively, which use biotin as a linking group between the antibody and streptavidin or avidin.

In another embodiment of the present invention, the target-specific agent and biotinylated compound are administered to the host as a pharmaceutical composition in an amount sufficient for the desired therapeutic or diagnostic effect. The pharmaceutical compositions comprise an effective dosage of at least one biotinylated compound according to the present invention together with a pharmaceutically acceptable carrier. The compounds an be administered by well-known routes including oral, intravenous, intramuscular, intranasal, intradermal, subcutaneous, parenteral and the like. Depending on the route of administration, the pharmaceutical compositions may require protective coatings.

The pharmaceutical forms suitable for injectionable use include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water, buffered aqueous solutions (i.e., biocompatible buffers), ethanol, polyol (glycerol, propylene glycol, polyethylene glycol and the like), suitable mixtures thereof, surfactants or vegetable oils. Sterilization can be accomplished by any art recognized technique, including but not limited to, addition of antibacterial or antifungal agents, for example, paraben, chlorobutanol, phenol, sorbic acid, thimerosal, and the like. Further, isotonic agents, such as sugars or sodium chloride may be incorporated in the subject compositions.

Production of sterile injectable solutions containing the subject contrast agent is accomplished by incorporating these agents in the required amount in the appropriate solvent with various ingredients enumerated above, as required, followed by sterilization, preferably filter sterilization. To obtain a sterile powder, the above solutions are vacuum-dried or freeze-dried as necessary.

When the biotinylated compounds are administered orally, the pharmaceutical composition thereof containing an effective dosage of the contrast agent, may also contain an inert diluent, an assimilable edible carrier and the like, be in hard or soft shell gelatin capsules, be compressed into tablets, or may be in an elixir, suspension, syrup or the like. Preferred compositions of the conjugated antibody provide effective dosages in the range of about 0.1–5 mg. In a preferred embodiment the effective dosage is about 1 mg. Preferred compositions of the biotinylated compounds provide effective dosages in the range of about 1–1000 μg. The preferred dosage range of biotinylated compounds is about 10–100 μg.

As used herein, a pharmaceutically acceptable carrier includes any and all solvents, dispersion media, coatings, antibacterial and antifungal agents, isotonic agents, and the like. The use of such media and agents are well-known in the art.

The present invention is also directed to a kit for diagnosis or therapy. In one embodiment, the kit is compartmentalized to receive a container adapted to contain a biotinylated compound of the present invention. In an exemplified use of the subject kit, the biotinylated compound is labeled with a radioactive nuclide or paramagnetic metal and administered to a patient hours to several days after administration of streptavidin or avidin-conjugated targeting agent.

In another embodiment, the kit is compartmentalized to receive a first container adapted to contain a biotinylated compound of the present invention, and a second container adapted to contain an avidin or streptavidin conjugated targeting agent. In an exemplified use of the subject kit, the contents of the second container are administered to a host. A metal chelating agent-containing biotinylated compound is labeled with a radioactive or paramagnetic metal and administered to the host hours to several days after the administration of the targeting agent.

The following examples further illustrate the invention.

EXAMPLE I

Synthesis and Analysis of Defero-desaminolysyl-biotin

This example provides, for comparative purposes, the synthesis of a biotinidase sensitive compound, i.e. a biotinylated compound that does not contain the novel linkage of the present invention. Biocytin was covalently linked to DFO by the following Scheme I, in which DFO was provided as its commercially available form, deferoxamine mesylate. Scheme I results in the synthesis of DLB, a covalent conjugate of DFO and biotin.

Scheme I

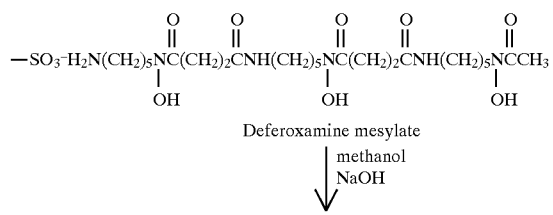

-continued
Scheme I

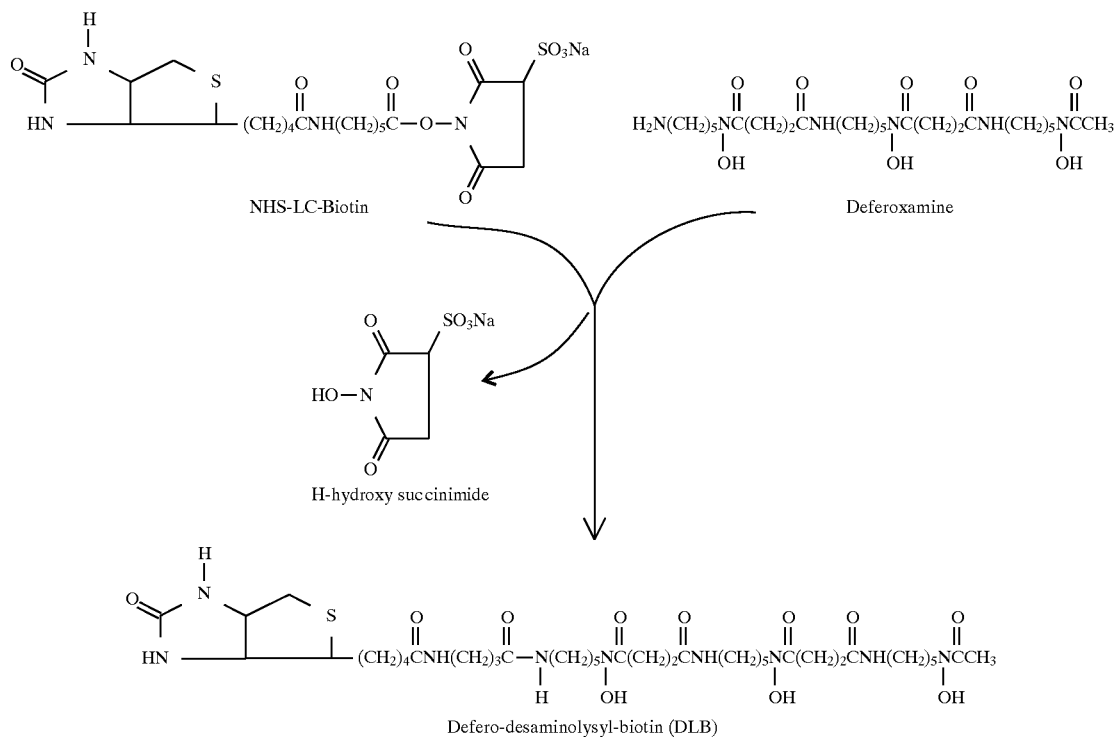

The synthesis of DLB according to Scheme 1 was accomplished as follows. Solid deferoxamine mesylate was added to methanol for a concentration of about 10 mM, followed by addition of NaOH to reach a final concentration of 10 mM NaOH. The solution was maintained at about 60°. Solid NHS-LC-biotin was added to the deferoxamine solution to reach a final molarity of 20 mM NHS-LC-biotin and incubated at least one hour at 60°. The preferred molar ratio of NHS-LC-biotin: deferoxamine mesylate is 2–5:1. DLB synthesized according to Scheme I was purified by standard methods known to the ordinarily skilled artisan, for example high performance liquid chromatography (HPLC).

To determine the in vitro stability of DLB, the avidin binding assay was used. DLB was labeled with $^{67}$Ga by direct addition of a $^{67}$Ga solution to DLB, followed by incubation at room temperature for one to several hours. Samples of radiolabeled DLB were added to 1 ml of saline or human plasma and then incubated at 37° for up to 24 hours. Aliquots of radiolabeled DLB were removed at various time points and tested for ability to bind avidin.

As shown in FIG. 1, when $^{67}$Ga-DLB was incubated at 37° in saline followed by a measurement of avidin binding activity as described above, approximately 85% of the $^{67}$Ga retained its avidin binding ability after 24 hours of incubation, indicating that the conjugate is stable in saline. It has been surprising found that after incubation in human plasma, $^{67}$Ga-DLB rapidly lost its avidin binding ability, with less than 50% of the radiolabel capable of binding avidin after 10 minutes of incubation in plasma, and less than 15% at 2 hours, demonstrating that the conjugate was rapidly dissociating under physiological conditions.

Figure 2:
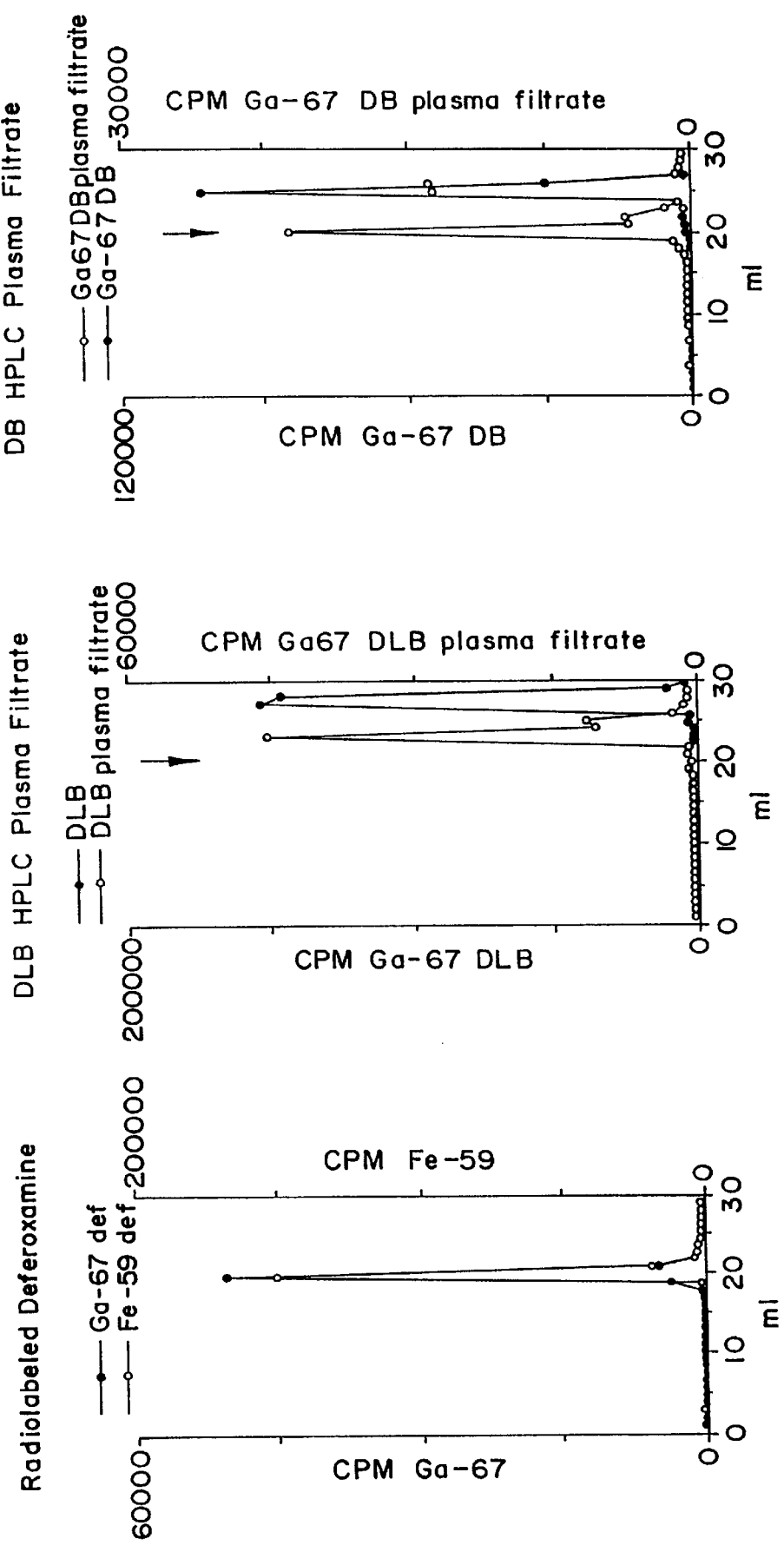
FIGS. 2A, 2B and 2C present HPLC profiles of radiolabeled DB and DLB following incubation in plasma. The radioactivity in the column effluent is plotted as a function of the eluting solvent volume.
Figure 3:
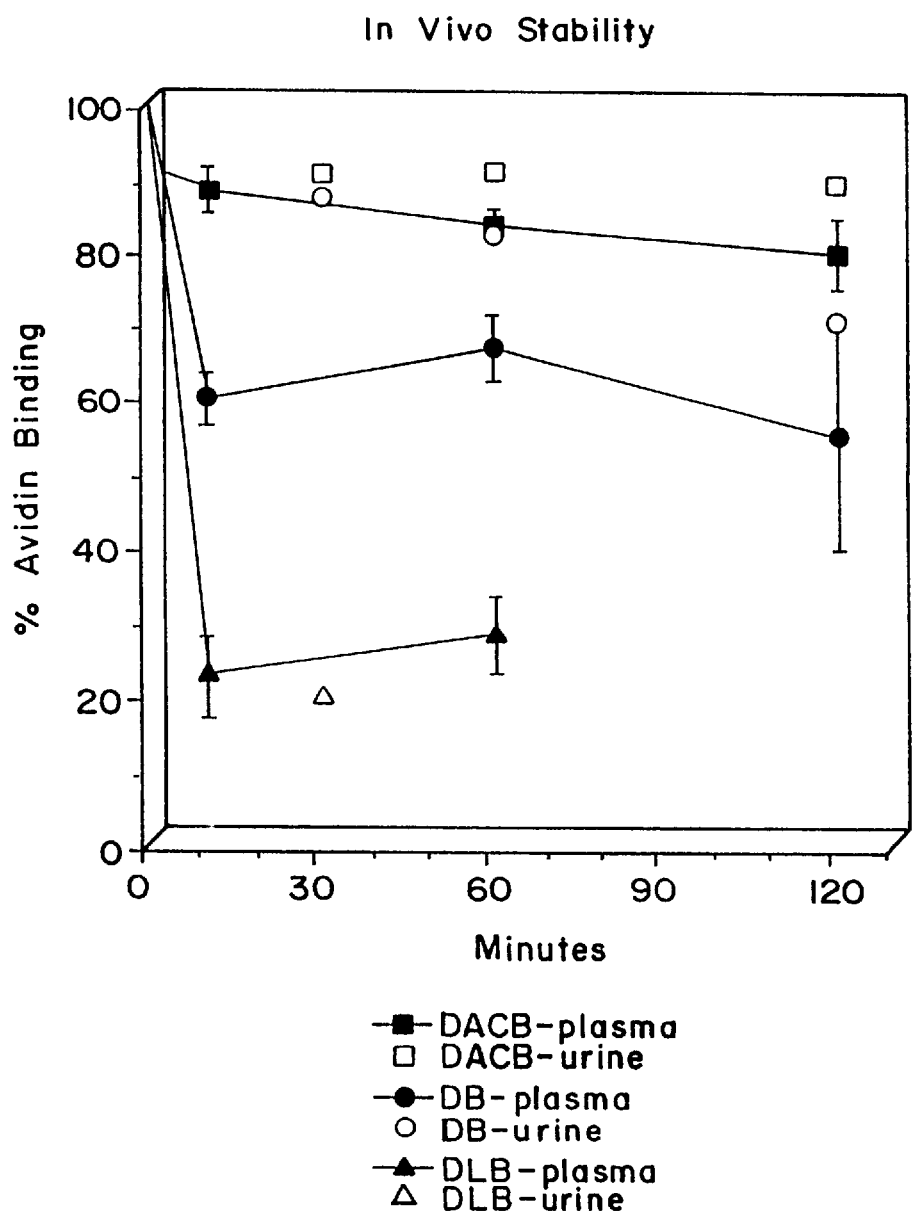
FIG. 3 is a graph of the percent of avidin binding ability retained by DACB, DB and DLB in plasma and urine samples following intravenous injection of the conjugates.

The in vivo stability of DLB was further assessed by intravenously injecting $^{67}$Ga-DLB, into dogs and then subjecting plasma and urine samples to the avidin binding assay. Blood was withdrawn at intervals after injection of $^{67}$Ga-DLB and dispensed into heparinized tubes for plasma analysis. Urine samples were obtained by flushing the bladder with saline approximately every thirty minutes. Avidin binding assays of the plasma and urine samples indicate that only about 20% of the radioactivity present in plasma and urine samples withdrawn at ten and thirty minutes, respectively, retained its ability to bind avidin. These results are shown in FIG. 3. This confirms results of in vitro studies and demonstrates that DLB is unstable in vivo. To further assess the stability of DLB, $^{67}$Ga-DLB was incubated in plasma at 37° for two hours and then subjected to chromatographic analysis by HPLC. The radioactivity in the column effluent was plotted as a function of the eluting solvent volume, and the HPLC elution profiles of unincubated radiolabeled DLB and DFO were compared to radiolabeled DLB which had been incubated in plasma. The chromatographic profile are depicted in FIGS. 2A, 2B and 2C. The major peak of radioactivity in the plasma-incubated sample eluted earlier than the major peak of the unincubated sample, indicating that DLB is unstable. However, the plasma-incubated sample did not co-elute with radiolabeled DFO, indicating that DLB had not simply dissociated into DFO and biocytin, but rather demonstrates that DLB was rapidly degraded in vivo to biotin and desaminolysyl-deferoxamine. Chromatographic analysis of urine samples from the in vivo experiments described above and shown in FIGS. 4A, 4B and 4C, confirms that, even after thirty minutes, radiolabeled DLB had been degraded to desaminolysyldeferoxamine.

EXAMPLE II

Synthesis and Analysis of Defero-Acetyl-Cysteinyl-Biotin

DACB was synthesized by covalently conjugating iodoacetyl-deferoxamine and N-cysteinyl-biotin by the following Scheme II.

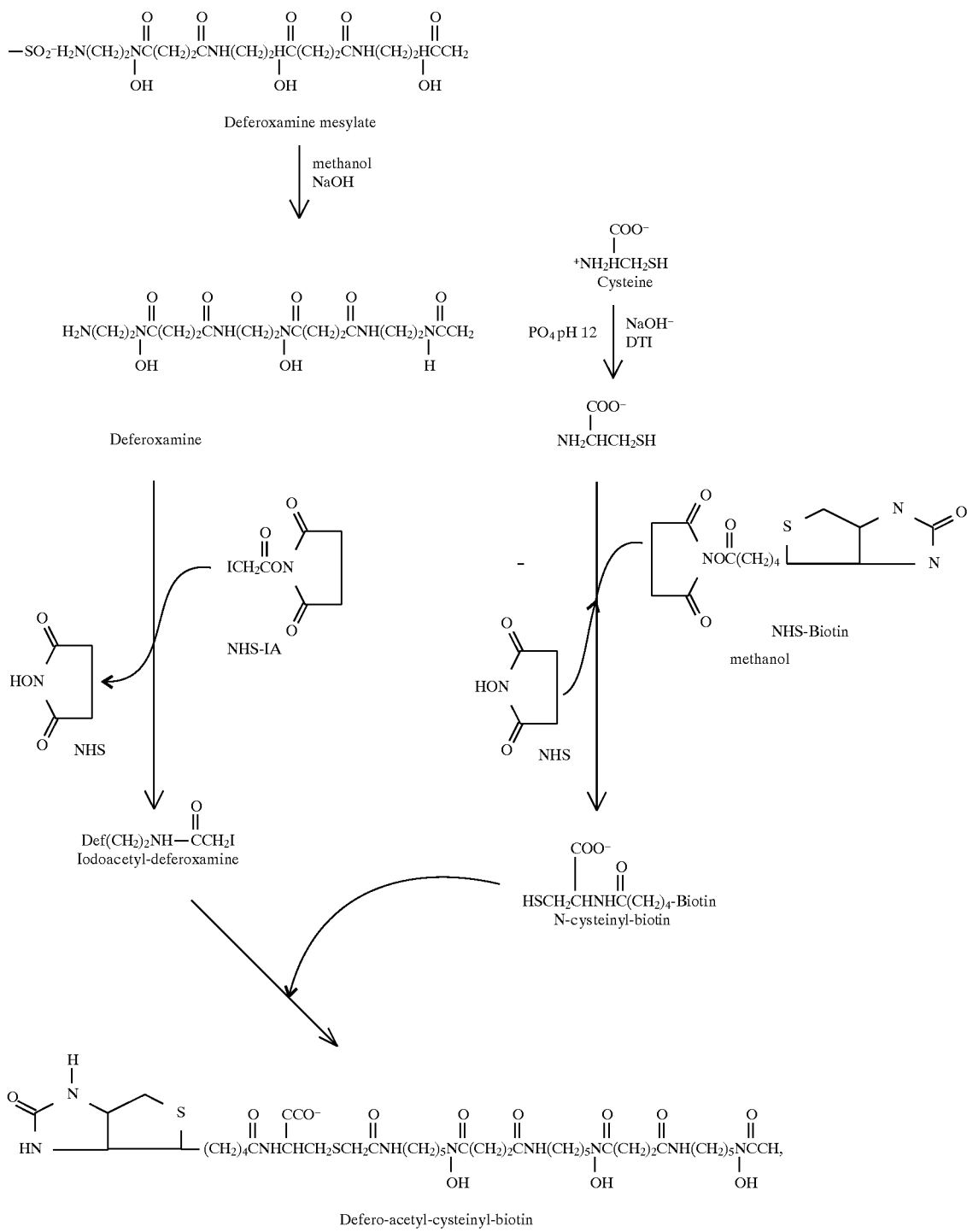

Scheme II

Solid deferoxamine mesylate was added to methanol for a concentration of 20 mM, followed by addition of NaOH to reach a final concentration of 20 mM NaOH. The solution was heated and maintained at 65°. Solid iodoacetic acid N-hydroxysuccinimide ester (NHS-IA) was added to the deferoxamine solution to a final molarity of 50mM NHS-IA and incubated for at least one hour at 65°. The resulting iodoacetyl-deferoxamine (IA-DFO) was purified by HPLC with an EM LiChroCART reverse phase column using a linear gradient of 0–10 ml 100% Buffer A (0.025M phosphate, pH 6, 2 mM NTA) and 10–60 ml 0–100% Buffer B (0.025M phosphate, pH 6, 2 mM NTA, 75% methanol). IA-DFO, but not unconjugated DFO, has an absorbance at 260 nm and thus was purified by measuring the absorbance of the eluate and collecting the fraction with absorbance at 260 nm.

To prepare cysteinyl-biotin, 60–120 mM DTT was added to cysteine in 0.05M phosphate buffer for a final concentration of 60 mM cysteine. NHS-biotin was solubilized in methanol at a concentration of 20 mM and heated to 60°. Equal volumes of the cysteine and NHS-biotin solutions were mixed and incubated at 65°. The preferred molar ratio of cysteine:NHS-biotin is 2–10:1. The resulting cys-biotin was purified by HPLC. The fraction containing cys-biotin was identified by its reactivity with 5,5'-dithiobis-(2-nitrobenzoic acid), (DTNB; Ellman's reagent). Ellman's reagent is used to detect thiols and reacts with cys-biotin but not with free biotin, which does not contain a free SH group.

The pH of purified cys-biotin and IA-DFO was adjusted to 7.5 with NaOH. Cys-biotin and IA-DFO were mixed and incubated overnight. The preferred molar ratio of cys-biotin:IA-DFO was 2:1. The resulting DACB was purified by HPLC using the column and gradient parameters described above for the HPLC purification of IA-DFO.

To determine the in vitro stability of DACB, the avidin binding assay was used. DACB was first labeled with $^{67}$Ga plotted as a function of the eluting solvent volume, and the HPLC elution profiles of uninjected radiolabeled DACB and DFC were compared to radiolabeled DACB in urine samples.

In samples obtained at 30 minutes, all of the radioactivity present co-eluted with the radioactivity in uninjected DACB, confirming that DACB has excellent stability in vivo.

EXAMPLE III

In Vitro Stability of DLB, DB and DACB

The in vitro stability of DACB was compared with two compounds that do not contain the novel linkage of the present invention. DLB is described in Example I. Defero-biotin (DB) is a covalent conjugate of DFO and biotin having the formula:

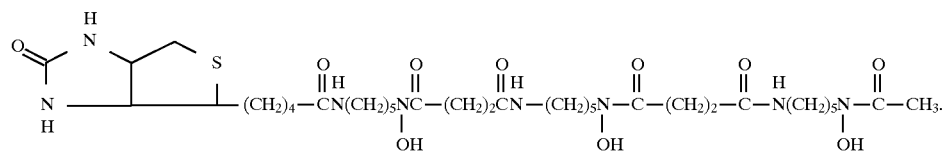

by direct addition of a $^{67}$Ga solution to DACB, followed by incubation at room temperature for one to several hours. Samples of radiolabeled DACB were added to 1 ml of saline or human plasma and then incubated at 37° for up to 24 hours. Aliquots of radiolabeled DACB were removed at various time points and tested for ability to bind avidin.

When $^{67}$Ga-DACB is incubated at 37° in saline followed by a measurement of avidin binding activity as described above, approximately 95% of the $^{67}$Ga retained its avidin binding ability after 24 hours of incubation, indicating that the conjugate is extremely stable in saline. After incubation in human plasma for six hours, approximately 95% of the $^{67}$Ga-DACB remained bound to avidin. After 24 hours, approximately 80% of the radiolabel remained capable of associating with avidin in the avidin binding assay, indicating the excellent stability of DACB in plasma.

The in vivo stability of DACB was evaluated by intravenously injecting $^{67}$Ga-DACB, into dogs and then subjecting plasma and urine samples to the avidin binding assay as described above. This assay demonstrates that approximately 95% and 85% of the radioactivity present in urine and plasma samples, respectively, withdrawn at 60 minutes retained ability to bind avidin. This confirmed the results of the in vitro studies and demonstrated that DACB is extremely stable in vivo and thus suitable for applications in in vivo imaging and therapy.

The stability of DACB was further evaluated by examining the urine samples obtained after intravenous injection of radiolabeled DB for the presence of DB, DFO and other possible metabolites were by HPLC. Urine samples for HPLC analysis can be obtained by injecting radiolabeled DACB into dogs and obtaining urine samples by flushing the bladder at various time intervals. Urine samples were obtained at 30 minutes, 2 hours, and 4 hours and analyzed by HPLC. The radioactivity in the column effluent was DLB, DB and DACB were each labeled with $^{67}$Ga by direct addition of a $^{67}$Ga citrate solution (specific activity of 50–500 μCi/μg of $^{67}$Ga) followed by incubation overnight at room temperature. Samples of each radiolabeled conjugate were added to 1 ml of saline and 1 ml of dog plasma and incubated at 37° C. for 26 hours. 100 μl aliquots of the radiolabeled conjugates were removed at various time points and assessed by the avidin binding assay.

Each radiolabeled conjugate was incubated with 100 μg avidin for 1–10 minutes at room temperature on a centricon 30 filter. Filters were counted in a gamma counter, washed with PBS, pH 7.5, and centrifuged at 4000–5000 g for 20 minutes for saline samples and 30 minutes for plasma samples. After washing/centrifugation, filters were again counted. The ratio of counts per minute (cpm) after centrifugation to before centrifugation was calculated. A ratio of 1 represents 100% avidin binding ability retained after incubation. Results are plotted as percent avidin binding ability per unit time and shown in FIG. 1.

Plasma filtrates of DLB and DB were analyzed by HPLC and compared to the HPLC profiles of $^{67}$Ga- and $^{59}$Fe-labeled DFO. Results are shown in FIGS. 2A, 2B and 2C. The profiles of $^{67}$Ga-DFO and $^{59}$Fe-DFO, which are identical, are shown in Panel A and indicated by the arrows in Panels B and C.

EXAMPLE IV

In Vivo Stability of DLB, DB and DACB

Figures 4A, 4B, 4C:
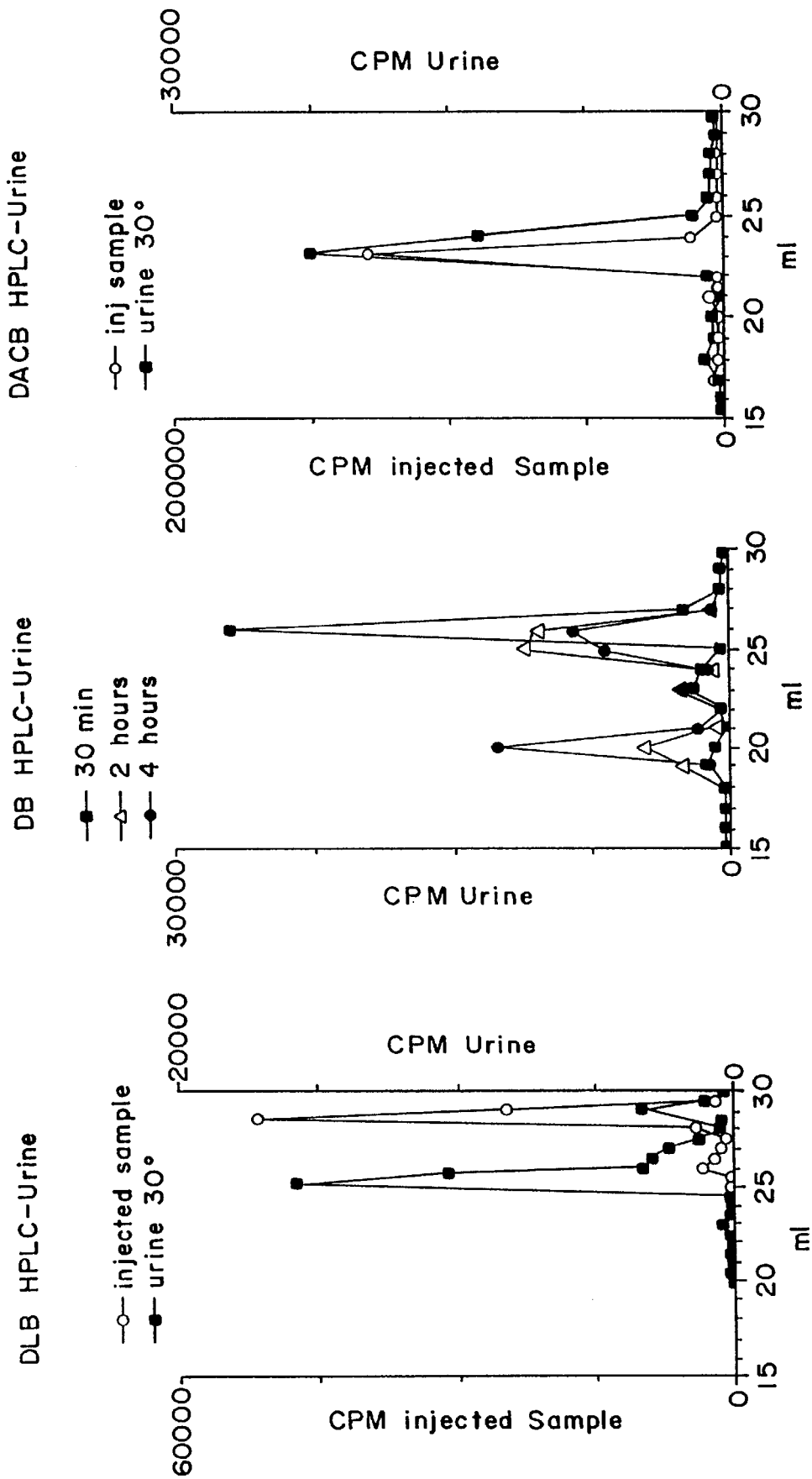
FIGS. 4A, 4B and 4C present HPLC profiles of urine samples obtained after intravenous injection of radiolabeled DLB, DB and DACB.

DLB, DB and DACB were labeled with $^{67}$Ga as described in Example 1 and counted in a gamma counter. Each radiolabeled compound (1.2 μg DLB, 5 μg DB or 5 μg DACB) was intravenously injected into a dog. Whole blood was taken at 10, 60 and 120 minutes after injection and dispensed into heparinized tubes. Urine samples were obtained by flushing the bladder with 100 ml saline at 30, 60 and 120 minutes. Avidin binding was assessed and graphed as described in Example I. Results are shown in FIG. 3. Urine samples obtained 30 minutes, 2 hours and 4 hours after radiolabeled DB injection, and 30 minutes after radiolabeled DACB injection were analyzed by HPLC as described in Example I and compared to the HPLC profiles of the labeled compounds before injection. Results are depicted in FIGS. 4A, 4B and 4C.

EXAMPLE V

Pharmacokinetics of $^{67}$Ga-DACB

The basic in vivo pharmacokinetic parameters of $^{67}$Ga-DACB were examined as follows.

$^{67}$Ga-DACB was intravenously injected to dogs at a dose of 5 μg and the blood clearance and urinary excretion monitored. Whole blood was taken at intervals after iv injection placed in pre-weighed tubes. The pharmacokinetics were determined using the R-Strip curve fitting program (Micromath, Salt Lake City, Utah). Blood was also dispensed into heparinized tubes for plasma analysis. To determine urinary excretion of $^{67}$Ga-DACB in the dog, the bladder was flushed with approximately 30 ml of saline every 30 minutes. Total accumulated radioactivity per time increment (30 minutes) was determined by multiplying sample counts by the total volume of urine collected.

Figure 5A:
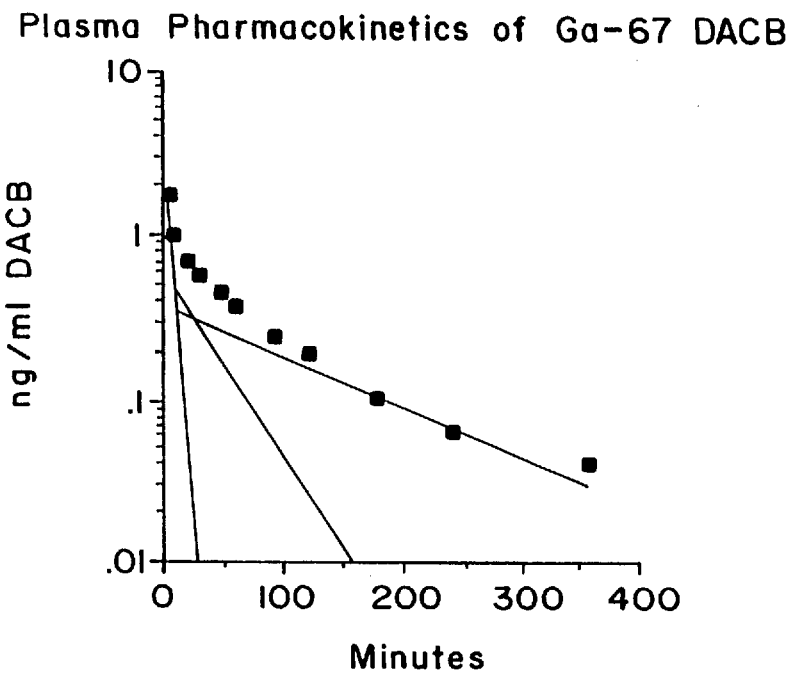
FIG. 5A demonstrates the plasma pharmacokinetics of $^{67}$Ga-DACB.
Figure 5B:
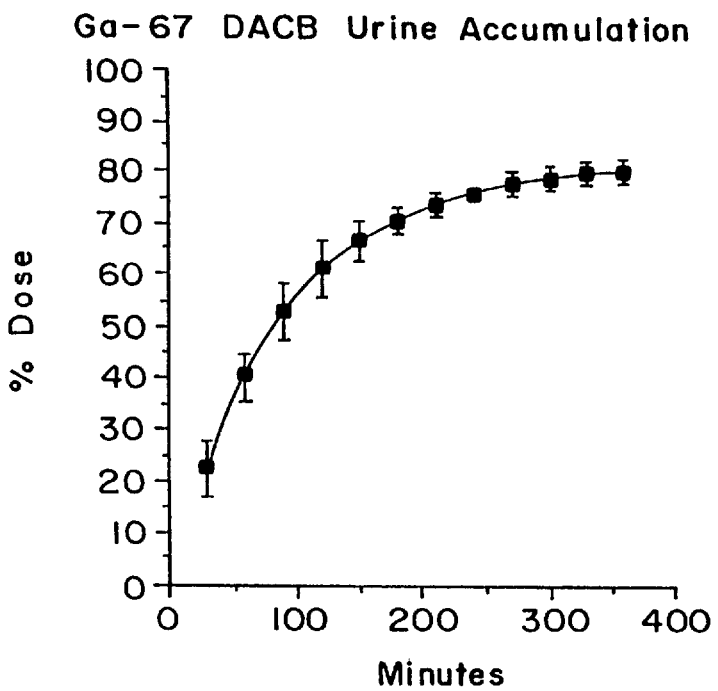
FIG. 5B depicts the urine accumulation of $^{67}$Ga-DACB.

As indicated in FIG. 5, Panel A, the plasma pharmacokinetics of DACB are best fit by a three exponential fit, typical of small radioactive chelates. As indicated in FIG. 5, Panel B, at 100 minutes after injection, 50% of DACB had accumulated in the urine, while at 6 hours 80% of DACB had accumulated in the urine.

EXAMPLE VI

Synthesis and Analysis of BEBH, BLEBH, BCEBH

A biotinylated Bolton Hunter reagent containing the novel linkage of the present invention (BCEBH) was synthesized and compared to two biotinylated Bolton Hunter reagents that do not contain the novel linkage of the invention (BEBH and BLECBH).

Biotinyl-aminoethyl-Bolton Hunter (BEBH) was synthesized by reacting NHS-biotin and ethylene diamine at pH 8.5 for one hour at a molar ratio of 1:10 to provide biotinyl-ethylamine. NHS-Bolton Hunter was added to purified biotinyl-ethylamine at pH 9.5 for one hour at a molar ratio of 1:1. BEBH was covalently labeled with $^{125}$I by a commercially available iodobead method (Pierce) and purified by HPLC. BEBH has the formula:

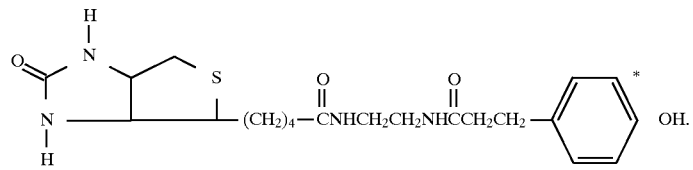

wherein * represents the site for $^{125}$I labeling.

Biotinyl-lysyl-ethyl-Bolton Hunter (BLEBH) contains a lysyl and ethyl group to provide the linkage between BH and biotin. BLEBH was prepared by reacting NHS-LC-biotin and ethylenediamine at pH 8.5 for one hour at a molar ratio of 1:10 to provide biotinyl-lysyl-ethamine. NHS-Bolton Hunter was added to HPLC purified biotinyl-lysyl-ethylamine at pH 9.5 for one hour at a molar ratio of 1:1. BEBH was covalently labeled with $^{125}$I by a commercially available iodobead method (Pierce) and purified by HPLC. The resulting BLEBH has the formula:

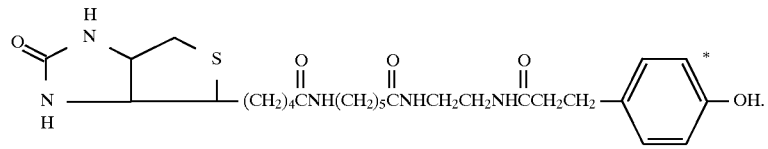

wherein * represents the site for $^{125}$I labeling.

Biotinyl-cysteinyl-aminoethyl-Bolton Hunter (BCEBH) contains the novel linkage of the present invention and was prepared according to the following Scheme III.

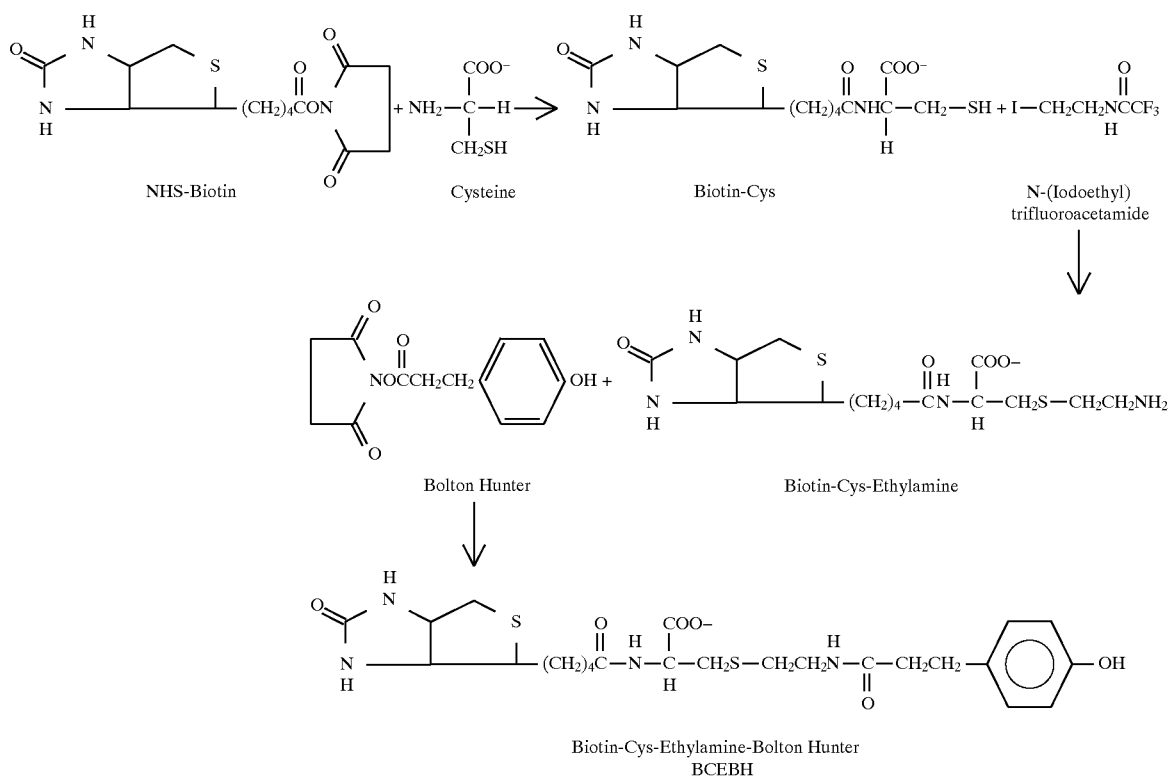

Biotin-Cys-Ethylamine-Bolton Hunter
BCEBH

Ten mg NHS-biotin was added 0.5 ml of a solution containing cysteine (50 mg/ml) in 0.05M phosphate buffer, pH 9.5 and incubated at pH at 8.5 for one hour at room temperature. Fifty mg DTT was added to break the disulfide bonds that might form with cysteine as a side reaction. The preferred molar ratio of cysteine to NHS-biotin was 10:1. The resulting Biotin-Cysteine conjugate was purified by reverse phase HPLC using a RP-Select B (4×250 mm) LiChroCART column (EM Science), Buffer A (0.05 M $Na_2PO_4$, monobasic, pH 6.5), Buffer B (A with 75% methanol) at a flow rate of 1 ml/min. and a linear gradient of 0% B for 0–5 ml and 0–100% B for 5–30 ml. Purity was assessed by the addition of Ellman's reagent, dithionitrobenzoic acid, which is used to detect the presence of free thiols. To a 4.5 ml pool of the purified Biotin-Cysteine conjugate was added 100 mg aminoethyl-8 (Pierce), followed by incubation overnight at 50°C., pH 8.5. The preferred molar ratio of aminoethyl-8 to Biotin-cysteine was 10:1. The resulting Biotincysteinylethylamine conjugate was purified by reverse phase HPLC as described above, and the purity of the Biotin-Cysteine-ethylamine conjugate was assessed by ninhydrin staining, which detects the presence of free amines.

Ten mg of NHS-Bolton Hunter was added to the Biotinyl-Cysteinyl-ethylamine conjugate, and the pH was maintained at 9.5, 50° C. for one hour. The preferred molar ratio of NHS-Bolton Hunter to Biotin-Cysteine-ethylamine was 1:1. $^{125}I$ labelling was performed as described above. The purified peak had an absorbance at 275 nm. The final concentration was determined spectrophotometrically using an assumed extinction coefficient of 1400 at 275 nm for a 1M solution, which is the extinction coefficient for a similar reagent, tyrosine.

Figure 6:
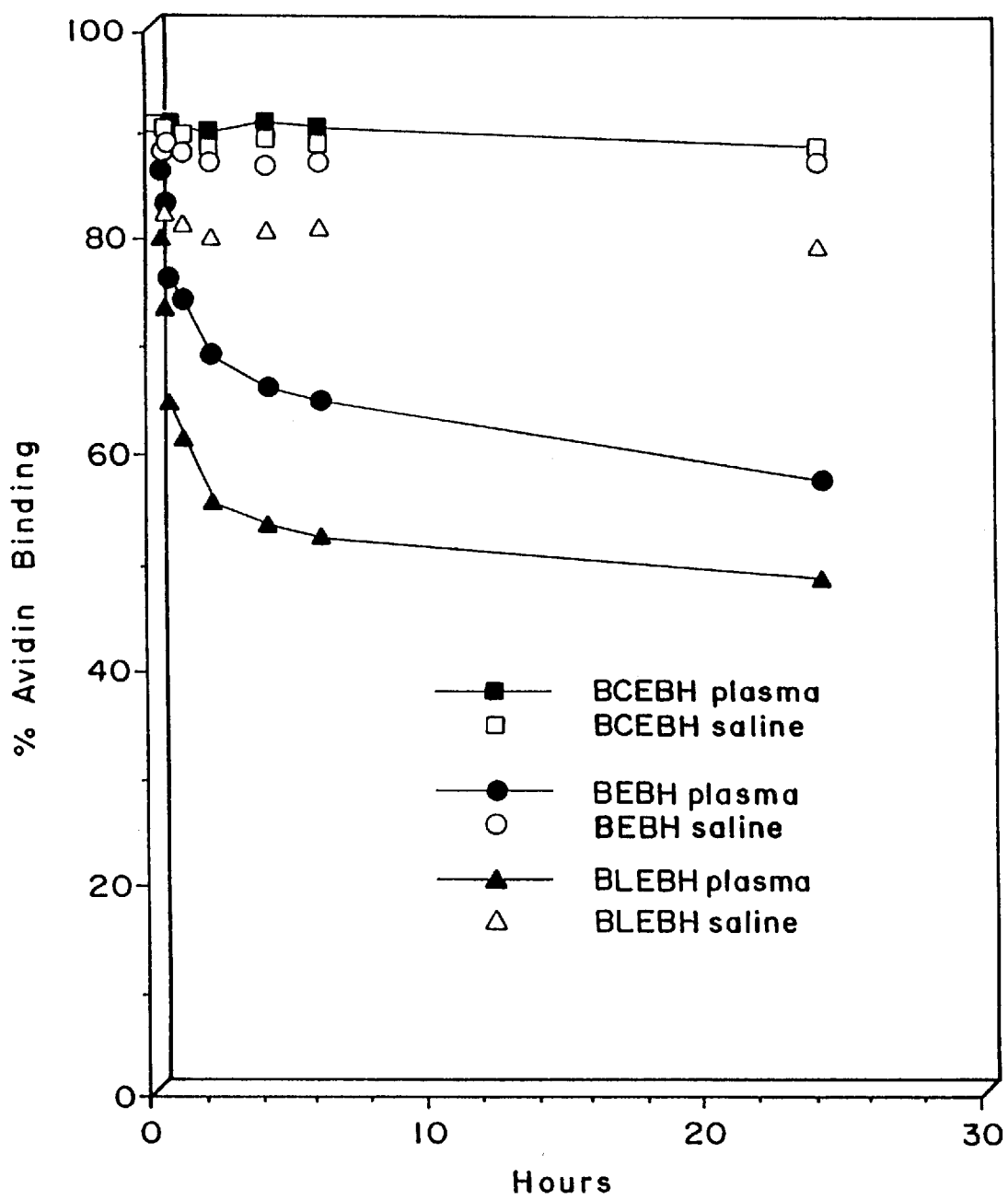
FIG. 6 is a graph of the percent of avidin binding ability retained by Biotinyl-Aminoethyl-Bolton Hunter (BEBH), Biotinyl-Lysyl-Ethyl-Bolton Hunter (BLEBH) and Biotinyl-Cysteinyl-Aminoethyl-Bolton Hunter (BCEBH) following incubation in plasma and saline.

Samples of BEBH, BLEBH and BCEBH were incubated in saline or plasma at 37° C. for 24 hours. Aliquots of the radiolabeled compounds were removed at various time points and tested for ability to bind avidin as described above. As demonstrated by the results presented in FIG. 6, BEBH, BLEBH and BCEBH are each stable in saline. After incubation for 24 hours in plasma, both BEBH and BLEBH exhibit marked reductions in avidin binding ability, indicating that the stability of these compounds in plasma is greatly reduced. In contrast, when BCEBH is incubated in plasma for 24 hours at 37° C., approximately 90% of the radiolabel remains associated with avidin, indicating that BCEBH exhibits excellent stability in plasma.

$^{125}I$ labelled BEBH, BLEBH and BCEBH can also be synthesized by carrying out the foregoing syntheses with commercially available pre-iodinated Bolton Hunter reagent.

We claim:

1. A compound having the formula:

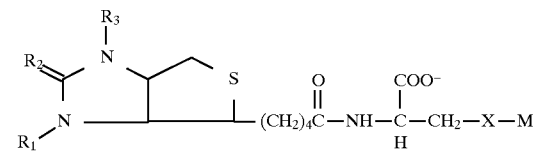

wherein the negative charge on the carboxylate is balanced by a cation; and wherein $R_1$ and $R_3$ are independently hydrogen, carboxyl or lower alkyl; $R_2$ is O or NH; X is S, a chemical bond or a linking group and M is selected from the group consisting of a chelating agent, a halogenating agent, a MRI agent, an enzyme, a lectin, a therapeutic agent selected from the group consisting of methotrexate, vinblastine, doxorubicin, bleomycin, cisplatinum, urokinase and tissue plasminogen activator, a fluorophore and a toxin selected from the group consisting of abrin, ricin, modeccin, Pseudomonas exotoxin A, diphtheria toxin, pertussis toxin and Shiga toxin.

2. A compound of claim 1 wherein $R_1$ is H, $R_2$ is O, $R_3$ is H and X is S-Y wherein Y is a chemical bond, acetyl group or a C1–C6 alkylene chain.

3. A compound of claim 1 or 2 wherein M is a chelating agent.

4. A compound of claim 3 wherein said chelating agent is selected from the group consisting of deferoxamine (DFO), diethylene-triaminopentaacetic acid (DTPA), ethylenediaminetetra-acetic acid (EDTA), bis-aminothiol (BAT, $N_2S_2$), ethylenediamine-di(O-hydroxyphenylacetic acid) (EDHPA), 2,2-dipyridyl (DIPY), polyaminopolycarboxylate, tetra-azacyclododecane tetracetate (DOTA), dithiocarbamate, dithiosemicarbazone (DTS), tetraazacyclotetradecane-tetracetate (TETA), hydroxamic acid derivatives and porphyrins.

5. The compound of claim 3 wherein said chelating agent is complexed with a metal.

6. A compound of claim 5 wherein said metal is selected from the group consisting of Tc-99m, $^{67}$Ga, $^{68}$Ga, $^{111}$In, $^{90}$Y, $^{186}$Re, $^{188}$Re, $^{212}$Bi, Fe, $^{52}$Fe and Gd.

7. A compound of claim 1 or 2 wherein M is a halogenating agent.

8. A compound of claim 7 wherein said halogenating agent is selected from the group consisting of tyramine, aniline, Bolton Hunter reagent and stannane.

9. The compound of claim 7 wherein said halogenating agent is covalently bound to a halogen.

10. A compound of claim 9 wherein said halogen is selected from the group consisting of radioisotopes of Cl, Br, I, F and At.

11. A compound of claim 9 wherein said halogen is selected from the group consisting of $^{211}$At, $^{77}$Br, $^{123}$I, $^{125}$I and $^{131}$I.

12. A compound of claim 11 or 2 wherein M is a toxin.

13. A compound of claim 1 or 2 wherein M is a therapeutic agent.

14. A compound of claim 1 or 2 wherein M is a fluorophore.

15. A compound of claim 14 wherein said fluorophore is selected from the group consisting of fluorescein, coumarin, rhodamine, phycoerythrin and Texas Red.

16. A compound of claim 1 or 2 wherein M is an enzyme.

17. A compound of claim 16 wherein said enzyme is selected from the group consisting of alkaline phosphatase, horseradish peroxidase, β-galactosidase and glucose oxidase.

18. A compound having the formula:

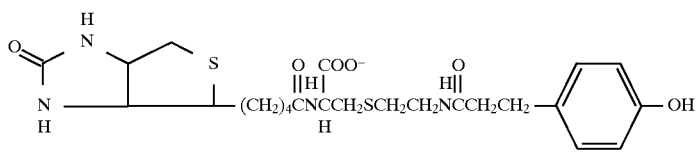

wherein the negative charge on the carboxylate is balanced by a cation.

19. A pharmaceutical composition comprising the compound of claim 1 and a pharmaceutically acceptable carrier.

20. A pharmaceutical composition comprising the compound of claim 5 and a pharmaceutically acceptable carrier.

21. A pharmaceutical composition comprising the compound of claim 9 and a pharmaceutically acceptable carrier.

22. A compartmentalized kit for diagnosis or therapy adapted to receive a first container adapted to contain the compound of claim 1.

23. A compartmentalized kit for diagnosis or therapy adapted to receive a first container adapted to contain the compound of claim 1 and a second container adapted to contain an avidin or streptavidin conjugated targeting agent.

24. The kit of claim 23 wherein said targeting agent is selected from the group consisting of monoclonal antibodies, polyclonal antibodies, chimeric antibodies, $F_v$ fragments, single chain antibodies, molecular recognition units and synthetic proteins and peptides.

25. A compound having the formula:

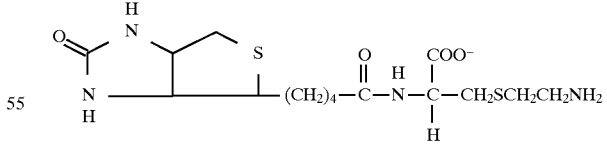

wherein the negative charge on the carboxylate is balanced by a cation.

* * * * *

UNITED STATES PATENT AND TRADEMARK OFFICE
CERTIFICATE OF CORRECTION

PATENT NO.   : 5,807,879
DATED        : September 15, 1998
INVENTOR(S)  : Scott F. Rosebrough It is certified that error appears in the above-identified patent and that said Letters Patent is hereby corrected as shown below:

Title page, [56] References Cited,
OTHER PUBLICATIONS: "196" should read -- 1796 --

Column 3,
Line 63, insert -- wherein the negative charges on the carboxylate is balanced by a cation and --

Column 4,
Line 13, insert -- wherein the negative charge on the carboxylate is balances by a cation --

Column 5,
Line 19, "fr" should read -- for --

Column 6,
Line 23, insert -- wherein the negative charge on the carboxylate is balanced by cation --

Column 9,
Line 49, insert -- wherein the negative charge on the carboxylate is balanced by cation --

Column 10,
Line 16, "HS" should read -- NHS --

Column 11,
Line 7, insert -- wherein the fragment has a positive charge to balance the negative charge on the carboxylate --
Line 54, "he" should read -- the --

UNITED STATES PATENT AND TRADEMARK OFFICE
CERTIFICATE OF CORRECTION

PATENT NO.   : 5,807,879
DATED        : September 15, 1998
INVENTOR(S)  : Scott F. Rosebrough It is certified that error appears in the above-identified patent and that said Letters Patent is hereby corrected as shown below:

Column 27, Claim 12,
Line 59, "11 or 2" should read -- 1 or 2 --

Signed and Sealed this

Eighteenth Day of September, 2001

*Attest:*

*Attesting Officer*

NICHOLAS P. GODICI
*Acting Director of the United States Patent and Trademark Office*